United States Patent
Slack et al.

(10) Patent No.: US 12,377,028 B2
(45) Date of Patent: Aug. 5, 2025

(54) PEROXYGEN-BASED SKIN DISINFECTANTS EFFECTIVE AGAINST MYCOBACTERIA AND YEASTS

(71) Applicant: Diversey, Inc., Fort Mill, SC (US)

(72) Inventors: Matthew Alasdair Timothy Slack, Ashbourne (GB); Faraz Alderson, Oakville (CA)

(73) Assignee: Diversey, Inc., Fort Mill, SC (US)

( * ) Notice: Subject to any disclaimer, the term of this patent is extended or adjusted under 35 U.S.C. 154(b) by 513 days.

(21) Appl. No.: 17/780,168

(22) PCT Filed: Dec. 2, 2020

(86) PCT No.: PCT/US2020/062794
§ 371 (c)(1),
(2) Date: May 26, 2022

(87) PCT Pub. No.: WO2021/113292
PCT Pub. Date: Jun. 10, 2021

(65) Prior Publication Data
US 2022/0401320 A1    Dec. 22, 2022

Related U.S. Application Data

(60) Provisional application No. 62/942,980, filed on Dec. 3, 2019.

(51) Int. Cl.
| | |
|---|---|
| *A61K 8/22* | (2006.01) |
| *A61K 8/24* | (2006.01) |
| *A61K 8/34* | (2006.01) |
| *A61K 8/41* | (2006.01) |
| *A61K 8/60* | (2006.01) |
| *A61Q 17/00* | (2006.01) |

(52) U.S. Cl.
CPC .................. *A61K 8/22* (2013.01); *A61K 8/24* (2013.01); *A61K 8/34* (2013.01); *A61K 8/41* (2013.01); *A61K 8/602* (2013.01); *A61Q 17/005* (2013.01); *A61K 2800/43* (2013.01); *A61K 2800/51* (2013.01)

(58) Field of Classification Search
CPC ... A61K 8/22; A61K 8/24; A61K 8/34; A61K 8/41; A61K 8/602; A61K 2800/43; A61K 2800/51; A61Q 17/005; A01N 37/16; A01N 59/00
See application file for complete search history.

(56) References Cited

U.S. PATENT DOCUMENTS

| | | | |
|---|---|---|---|
| 8,871,807 B2 | 10/2014 | Gohl et al. | |
| 10,646,607 B2 | 5/2020 | Lei et al. | |
| 2005/0255172 A1 | 11/2005 | Omidbakhsh | |
| 2013/0089533 A1 | 4/2013 | Zhu et al. | |
| 2013/0259823 A1 | 10/2013 | Omidbakhsh | |
| 2018/0235231 A1* | 8/2018 | Ahmadpour | ........... A01N 59/00 |

FOREIGN PATENT DOCUMENTS

| | | | | |
|---|---|---|---|---|
| CN | 107072212 A | | 8/2017 | |
| WO | WO-2012116744 A1 * | | 9/2012 | ............. A01N 25/00 |

OTHER PUBLICATIONS

Prado et al. (J Appl Oral Sci 2015;23(2):158-63). (Year: 2015).*
International Search Report and Written Opinion of Application No. PCT/US2020/062794 mailed Mar. 19, 2021; 12 pages.

* cited by examiner

*Primary Examiner* — Ernst V Arnold
(74) *Attorney, Agent, or Firm* — Lorenz & Kopf LLP

(57) ABSTRACT

An aqueous skin-compatible antimicrobial solution effective against yeasts and mycobacteria, comprises 2-3.8 wt % of at least one peroxygen; from 1.5 up to 7 wt % of at least one aromatic monohydroxy alcohol selected from phenoxyethanol, phenethyl alcohol, cyclopentylmethanol, cyclohexylmethanol, benzyl alcohol, or any mixture thereof; from 0.5 up to 5 wt % of at least one high foaming amine oxide amphoteric surfactant; from 2 up to 10 wt % of at least one polyol-based skin conditioning agent; an effective amount of at least one pH adjusting agent for adjusting the solution pH to 2-3. The solution has a redox potential value from 220 to 280 mV, is readily biodegradable, and is free of aromatic carboxylic acids, inorganic salts, quaternary ammonium compounds, volatile aliphatic monohydroxy alcohols, other volatile organic compounds, halogen containing compounds, and other antimicrobial agents.

20 Claims, No Drawings

PEROXYGEN-BASED SKIN DISINFECTANTS EFFECTIVE AGAINST MYCOBACTERIA AND YEASTS

CROSS-REFERENCE TO RELATED APPLICATION

This application is a National Phase of PCT International Application No. PCT/US2020/062794, filed on Dec. 2, 2020, which claims priority to U.S. Provisional Application No. 62/942,980, filed on Dec. 3, 2019; the content of these patent applications are incorporated by reference herein.

TECHNICAL FIELD

The present disclosure relates to antimicrobial compositions for use on skin.

BACKGROUND

A wide range of disinfectants is known, as discussed for example in Disinfection, Sterilization, and Preservation, edited and partially written by Professor Seymour S. Block, Fifth Edition, published 2001 by Lippincott Williams & Wilkins, Philadelphia. Certain peroxygen compounds, chlorine compounds, phenolics, quaternary ammonium compounds and surface active agents are known for their germicidal properties.

Peroxygen compounds, including hydrogen peroxide, are finding favor in many applications because their breakdown products, water and oxygen, are innocuous. Furthermore, they tend to have a broad spectrum of antimicrobial activity. Broad spectrum activity is important in situations where harmful organisms are present but their identity is not known.

A challenge in formulating peroxygen-based disinfecting compositions is to make them gentle enough for use on skin while providing adequate antimicrobial activity, especially against hard-to-kill microorganisms such as mycobacteria and yeasts. Another challenge is to make such products effective at contact times used in the real world. For example, some peroxygen-based disinfectants may take 30 minutes or more after application to disinfect a treated surface. In many circumstances, this rate of disinfection is far from satisfactory. Still a further challenge is to make such products aesthetically pleasing, for example, with desirable scents or odors.

Accordingly, there is a need for a peroxygen-based skin disinfectant that can kill a wide variety of organisms including the hardier yeasts and mycobacteria, at acceptable contact times, and which is aesthetically inoffensive, if not pleasing.

SUMMARY

The present disclosure provides compositions (in various forms or formats) for reducing the microbial load present on skin.

According to a first aspect, the disclosure provides a skin-compatible antimicrobial solution effective against both yeasts and mycobacteria, comprising, consisting essentially of, or consisting of at least one peroxygen compound in a concentration of from about 2 to about 3.8 wt %; at least one aromatic monohydroxy alcohol selected from the group consisting of phenoxyethanol, phenethyl alcohol, cyclopentylmethanol, cyclohexylmethanol, and benzyl alcohol in a concentration from about 1.5% up to about 7% wt; at least one high foaming amine oxide amphoteric surfactant in a concentration from about 0.5% up to about 5% wt; at least one polyol-based skin conditioning agent in a concentration from about 2% up to about 10%; an effective amount of at least one pH adjusting agent effective to adjust the pH of the solution to from about 2 to about 3; optionally, at least one additional ingredient selected from the group consisting of pigments and dyes, fragrances, rheology modifiers, foaming agents, other skin conditioning agents, softening agents, anti-wrinkling agents, odor removal/odor capturing agents, anionic surfactants, nonionic surfactants, buffering agents, builders, chelating agents/peroxygen stabilizers, radical scavengers, preservatives, soil shielding/soil releasing agents, ultraviolet light protection agents, and allergicides; and the balance of water. The solution has a redox potential value in the range of 220 to 280 mV, is readily biodegradable, and is free of aromatic carboxylic acids, inorganic salts, quaternary ammonium compounds, volatile aliphatic monohydroxy alcohols, other volatile organic compounds, halogen containing compounds, and other antimicrobial agents. By being "free" of these compounds is meant that these compounds are not intentionally added to the compositions and, if present, would be present only as impurities in an amount less than 0.1 wt %.

The composition can optionally contain additional ingredients such as fragrances, dyes, rheology modifiers, additional skin conditioning agents, foaming agents, buffering agents, chelating agents, emulsifiers, hydrotropes, solvents, amphoteric surfactants, and nonionic surfactants.

The disinfecting solution can be formulated in concentrated form wherein the ingredients are present in higher concentrations. Concentrates are more economical to transport and store due to their smaller weight and volume. Such concentrates can be diluted by the end user with water or another solvent to form ready-to-use solutions in accordance with the disclosure.

Concentrated version of the solution can have a pH ranging from about 0 to about 3. The skilled person will appreciate that the solutions can be made by combining multiple parts, with the parts being present in solid and/or liquid forms. Accordingly, other aspects of the disclosure relate to kits, products, or other variants that contain the compounds or ingredients disclosed herein either present together or separately. Water is therefore optional in some embodiments of the disclosure.

Embodiments of solutions in accordance with the disclosure are effective in passing known antimicrobial testing methods, e.g., without limitation, ASTM, EN, AOAC and OECD methods, and/or in reducing microbial populations on a surface by at least 1 $\log_{10}$, preferably at least 2, 3, 4, or 5 $\log_{10}$, using these methods.

Furthermore, in other aspects, the disclosure includes uses of the composition according to its various aspects, as well as methods of disinfection and sanitization. For example, the disclosure provides, according to another aspect, a method of reducing microbial populations on a surface contaminated with microorganisms, comprising applying an effective amount of the solution according to the first aspect to the surface for a contact time of at least about 10, 20, 30, 40, 50, 60, 70, 80, or 90 seconds, and/or up to about 10, 9, 8, 7, 6, or 5 minutes. In some embodiments, the disinfecting solution is effective to reduce the number of microorganisms on the surface by at least 1, 2, 3, 4, or 5 $\log_{10}$.

DETAILED DESCRIPTION

For the sake of clarity and to avoid ambiguity, certain terms are defined herein as follows.

The term "comprising" means "including without limitation." Thus, a composition comprising a list of ingredients may include additional ingredients not expressly recited. The term "consisting of" means "including the listed ingredients and such additional ingredients as may be present as natural or commercial impurities or additives." Natural and commercial impurities will be apparent to the person of ordinary skill in the art. An example of a commercial additive are minute quantities of stabilizers in hydrogen peroxide commercial solutions, for example. The term "consisting essentially of" means "consisting of" the listed ingredients (as defined herein) plus such additional ingredients as would not "materially affect" (positively or negatively) the basic and novel properties of the solution." By "basic and novel properties" is meant the antimicrobial efficacy of the solution, whether in terms of degree or rate of kill, or the number or identity of microorganisms against which the composition is effective. For the sake of clarity, a non-logarithmic difference in these parameters of ±50% would be deemed to be a "material effect."

The term "weight percent," "wt %," "percent by weight," "% by weight," % w/w, and variations thereof refer to the concentration of a substance as the weight of that substance divided by the total weight of the composition and multiplied by 100.

The term "about" refers to a variation in the numerical quantity that can occur, for example, through typical measuring and liquid handling procedures used for making concentrates or ready-to-use (RTU) solutions in the real world, through differences in the manufacture, source, or purity of the ingredients used to make the compositions or carry out the methods, and the like. The term "about" also encompasses amounts that differ due to different equilibrium conditions or different reaction levels for a composition resulting from a particular initial mixture. For the sake of clarity, term "about" includes variations in the expressed value of up to 5% (plus or minus). Whether a value is modified by the term "about" or not, the claims include equivalents to the values.

When used herein, the term "effective amount" means an amount that would bring about the desired effect, based on the known purpose and function of the ingredient and application of the composition. What constitutes an effective amount will be determinable by the person of ordinary skill in the art without having to engage in inventive experimentation.

In the description and claims, the singular forms "a," "an," and "the" include plural referents unless the content clearly dictates otherwise. Thus, for example, reference to a composition containing "a compound" includes a composition having two or more compounds. It should also be noted that the term "or" is generally employed in the sense of "and/or" unless the content clearly dictates otherwise.

The expression "redox potential" or "oxidation/reduction potential" (ORP) is the tendency of a chemical species (e.g. a solution) to acquire electrons (be reduced) or release electrons (be oxidized). Reduction potential is measured in volts (V), or millivolts (mV). Each solution has its own intrinsic reduction potential; the more positive the potential, the greater the solution's affinity for electrons and tendency to be reduced. Conversely, the more negative the potential, the greater the tendency to be oxidized. The term "standard reduction potential" is the oxidation/reduction potential measured under the following standard conditions: about 20° C. to about 25° C., a partial pressure of 1 bar for each gas that is part of the reaction, and using metals in their relatively pure state (it being recognized that most metals are not available in a 100% pure state). The standard reduction potential is defined relative to a standard hydrogen electrode (SHE) reference electrode, which is arbitrarily given a potential of 0.00 volts.

The redox potential of a composition indicates its reactiveness. The more negative or positive the redox potential value, i.e. the greater the difference from zero, the greater the tendency or likelihood that the solution participate in, or initiate, chemical reactions. The redox potential of a composition can be affected by many variables, such as its pH, peroxygen content, alkali or acid content, electrolyte content, and more.

It is believed that the higher the redox potential of a composition (such as a solution), the more effective it would be in inactivating microorganisms but also the harsher it would be on sensitive surfaces such as skin The inventors have developed compositions that possess a redox potential that make the compositions both effective against microorganisms, including the hardier types (mycobacteria and yeasts), and gentle on skin.

The present disclosure contemplates the possibility of omitting any components listed herein. The present disclosure further contemplates the omission of any components even though they are not expressly named as included or excluded from the disclosure.

All ranges recited herein include all values within the ranges though those values may not be expressly recited.

The chemical structures herein are drawn according to the conventional standards known in the art. Thus, where an atom, such as a carbon atom, as drawn appears to have an unsatisfied valency, then that valency is assumed to be satisfied by a hydrogen atom, even though that hydrogen atom is not necessarily explicitly drawn. The structures of some of the compounds of this disclosure include stereogenic carbon atoms. It is to be understood that isomers arising from such asymmetry (e.g., all enantiomers and diastereomers) are included within the scope of this disclosure unless indicated otherwise. That is, unless otherwise stipulated, any chiral carbon center may be of either (R)- or (S)-stereochemistry. Such isomers can be obtained in substantially pure form by classical separation techniques and by stereochemically-controlled synthesis. Furthermore, alkenes can include either the E- or Z-geometry, where appropriate. In addition, the compounds of the present disclosure may exist in unsolvated as well as solvated forms with acceptable solvents such as water, tetrahydrofuran, ethanol, and the like. In general, the solvated forms are considered equivalent to the unsolvated forms for the purposes of the present disclosure.

Unless otherwise specified, the term "alkyl" or "alkyl group" refers to hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups, etc.).

Unless otherwise specified, the term "alkyl" includes both "unsubstituted alkyls" and "substituted alkyls." The term "substituted alkyls" refers to alkyl groups having substituents replacing one or more hydrogens on one or more carbons of the hydrocarbon backbone. Such substituents may include, for example, alkenyl, alkynyl, halogena, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, am inocarbonyl, alkylam inocarbonyl, dialkylaminocarbonyl, alkylthiocarbonyl, alkoxyl, phosphate, phosphonate, phosphine, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including hetero aromatic) groups.

Peroxygen Compounds

The present composition comprises at least one peroxygen compound, such as hydrogen peroxide. The at least one peroxygen compound can be present in a concentration of from about 0.01, 0.1, 0.5, 0.8, 1, 1.5, 2, 2.5, 3, 3.5, or 4, and/or up to about 8, 7, 6, 5, 4.5, or 4 wt %.

When used herein, a "peroxygen compound" is a compound containing an oxygen-oxygen single bond or the peroxide anion:

Examples include alkali metal peroxides (e.g. sodium peroxide).

Also included are compounds that generate and release hydrogen peroxide when dissolved in aqueous solution (e.g. urea peroxide, perboric acid, sodium/potassium perborate, sodium persulfate, calcium peroxide, lithium peroxide, sodium peroxide, or other peroxides of alkali, alkaline earth, or transition group metals or salts thereof).

Still other examples are compounds according to the following formulas:

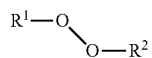

wherein $R^1$ and $R^2$ are independently a substituted or unsubstituted, branched or unbranched, cyclic or linear alkyl group. $R^1$ and $R^2$ may be connected to form a cyclic structure. Examples include dialkyl peroxides such as dibenzoyl peroxide, diacetyl peroxide, di(n-propyl) peroxydicarbonate, butyl peroxybenzoate, and many others commercially available under the brand name Luperox™. In certain cases, the $R^1$ and $R^2$ can be sulfurous or phosphorus atoms (e.g. peroxidisulfuric acid).

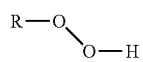

wherein R is H or a substituted or unsubstituted, branched or unbranched, cyclic or linear alkyl group. Examples include hydrogen peroxide, butyl hydroperoxide, ethylidene peroxide, ethyl hydroperoxide. In certain cases, the R can be sulfurous or phosphorus atoms (e.g. peroximonosulfuric acid).

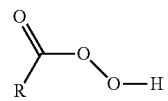

wherein R is a hydrogen, an oxygen, or a substituted or unsubstituted, branched or unbranched, cyclic or linear alkyl group. Examples include peroxycarboxylic acids (peracetic acid, peroctanoic acid, performic acid, peroxiphthalates, etc.), percarbonates (e.g. sodium percarbonates, potassium percarbonates), perbenzoic acid, cumene peroxide, and more.

Preferred peroxygen compounds are hydrogen peroxide, sodium peroxide, benzoyl peroxide, dibenzyl peroxides, peroxycarboxylic acids (peracetic acid, peroctanoic acid, performic acid, etc.), percarbonates (e.g. sodium percarbonates, potassium percarbonates), perborates, calcium peroxide, peroxymonosulfuric acid, and peroxydisulfuric acid.

Aromatic Alcohols

The present compositions also comprise an effective amount of at least one nonphenolic aromatic monohydroxy alcohol. Examples include phenethyl alcohol, benzyl alcohol, phenoxyethanol, cyclohexylmethanol and cyclopentylmethanol.

The at least one non-phenolic aromatic monohydroxy alcohol can be present in a concentration of from about 0.5, 1, 1.5, 2, 2.5, 3, 3.5, 4, 4.5, 5, 5.5, or 6 wt %, and/or up to about 15, 12, 10, 8, 7.5, 7, or 6.5 wt %.

Amphoteric Amine Oxide Surfactant

Compositions according to the disclosure also comprise at least one amphoteric amine oxide surfactant with a high foaming ability. These are those compounds having the formula R1R2R3NO wherein each of R1, R2, and R3 is independently a saturated, unsaturated, substituted or unsubstituted linear or branched alkyl group having from 1 to 28 carbon atoms, with at least one of R1, R2 and R3 having an alkyl chain length greater than eight carbons. Examples include lauramine oxide, N,N-dimethylundecylamine N-oxide, N,N-dimethylheptylamine N-oxide, cocamidopropylamine oxide, coamidomethylamine oxide, cocamine oxide, lauryl amidopropyl amine oxide, myristyl amidopropyl amine oxide, coco dipropylamine oxide, coco dimethylamine oxide, cetylamine oxide, decylamine oxide, isodecyloxypropylamine oxide, myristamine oxide, α,α'-[(oxidoimino)bis(methyl-2,1-ethanediyl]) bis[omega-hydroxypoly[oxy(methyl-2,1-ethanediyl]), N-[3-(C9-11-isoalkyl oxy)propyl] and its derivatives, tetradecyldimethylamine oxide, propoxy tallow amine oxides, and ethoxy tallow amine oxides.

These compounds can be used in a concentration of from about 0.5, 0.8, 1, 1.3, 1.5, 1.7, 2.0, 2.3, 2.5, 2.8, or 3 wt %, and/or up to about 15, 12, 10, 9, 8, 7, 6.5, 6, 5.5, 5, 4.5, 4, or 3.8 wt %.

Skin Conditioning Agents

The present compositions have at least one skin conditioning agent (also referred to as emollients or humectants) from the chemical class of polyols. Polyols, (also referred to as sugar alcohols) are aromatic, aliphatic, or polymeric compounds containing carbon and two or more hydroxyl groups. Examples of polyol-based skin conditioning agents include, without limitation, glycerol, glyceryl derivatives, polyglycerol, sorbitol, mannitol, erythritol, xylitol, arabitol, ribitol, dulcitol, lactitol, maltitol, d-panthenol, alkyl glucosides, and glycols (e.g., polyethylene glycols, propylene glycol, hexylene glycol, butylene glycol).

The present compositions can (optionally) include non-polyol skin conditioning agents, including, without limitation, di- or tri-glycerides, phospholipids, castor oil, allantoin, cationic polymers, lanolin and its derivatives, cetyl alcohol, ceramides, essential fatty acids such as linolenic acid, non-volatile monohydroxy alcohols, gamma-linolenic acid, linoleic acid, gamma-linoleic acid, tocopherols such as tocopheryl acetate, quaternised gums, quaternised polymers, glycerol ethers, ascorbates, glucose-ethers, vegetable oils, amino acids, and mineral oils.

The skin conditioning agent(s) collectively can be present in a concentration of from about 0.5, 1, 1.5, 2, 2.5, 3, 3.5, 4, 4.5, 5, 5.5, 6, or 6.5 wt %, and/or up to about 15, 12, 10, 9.5, 9, 8.5, 8, 7.5, 7, or 10 wt %.

pH Adjusting Agents

At least one acidic and/or alkaline pH adjusting agent must be present in a sufficient amount to adjust the pH to the desired value. In ready-to-use solutions, this value is from about 2, 2.1, 2.2, 2.3, 2.4, or 2.5 and/or up to about 3, 2.9, 2.8, 2.7, or 2.6. In concentrated solutions, this value is from about 0, 0.2, 0.5, 0.7, 1, or 1.2 and/or up to about 3, 2.5, 2, or 1.5. The skilled person will appreciate that the pH of the concentrated solution will depend on the level of concentration and be such that, when diluted to form a ready-to-use solution, the ready-to-use solution will have a pH ranging from about 2 to about 3 including any and all values in between.

Examples of acidic pH adjusting agents include, without limitation, inorganic acids, (e.g. phosphoric acid, hydrochloric acid, boric acid) and organic acids (e.g. citric acid, sulfosalicylic acid, sulfosuccinic acid, glycolic acid, lactic acid, formic acid, oxalic acid, malic acid, acetic acid, propionic acid, butanoic acid, pentanoic acid, hexanoic acid, heptanoic acid, octanoic acid, nonanoic acid, decanoic acid, undecanoic acid, dodecanoic acid, as well as their branched isomers, maleic acid, alpha-or-beta hydroxy-acetic acid, methane sulfonic acid, ethane sulfonic acid, propane sulfonic acid, butane sulfonic acid, xylene sulfonic acid, benzene sulfonic acid, toluenesulfonic acid, naphthalene disulfonic acid, neopentanoic acid, neoheptanoic acid, neodecanoic acid, malonic acid, succinic acid, glutaric acid, adipic acid, pimelic suberic acid).

Examples of alkaline pH adjusting agents include, without limitation, potassium hydroxide (KOH), sodium hydroxide (NaOH), triethanolamine, monoethanolamine, lithium hydroxide, magnesium hydroxide, calcium hydroxide, rubidium hydroxide, cesium hydroxide strontium hydroxide and barium hydroxide.

Other Amphoteric Surfactants

Other amphoteric surfactants can be included to further enhance the cleansing or foaming activity of the solution. Suitable amphoteric surfactants include alkyl amphocarboxylates, alkyl betaines, alkyl amidopropyl betaine amides, alkyl amidopropyl betaines, alkylsulfobetaines, amphoteric amine oxides, imidazolines, and derivatives thereof. Preferred imidazoline derivatives are alkylamphocarboxylates and alkyliminocarboxylates having the following structures

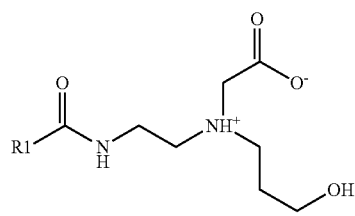

wherein R1 to R6 are each a saturated or unsaturated, substituted or unsubstituted linear or branched alkyl group having from 1 to 24 carbon atoms. These linear alkyl groups are each preferably a linear alkyl chain having 8 to 16 carbon atoms.

When used, these other amphoteric surfactants can be present in an amount from about 0.01, 0.5, 2.5, 5, 10, or 15 wt %, and/or up to about 20, 15, 10, 3, or 1 wt %.

Other Solvents

The present composition can include at least one additional solvent to further help solubilize the ingredients in the composition. When used, the additional solvent can be present in a concentration of from about 0.05, 0.5, 1, 5, 10, 15, 20, 25, 30, 40, or 50 wt % and/or up to about 85, 70, 60, 50, 40, 30, 25, 20, 10, or 5 wt %.

Examples include cyclic carbonates (e.g. propylene carbonate), dimethyl succinate, acetamidophenol, benzyl acetate, benzyl benzoate, acetanilide, acetophenone, 2-acetyl-1-methylpyrrole, essential oils (e.g., benzaldehyde, pinenes, terpineols, terpinenes, carvone, cinnamealdehyde, borneol and its esters, citrals, ionenes, jasmine oil, limonene, dipentene, linalool and its esters), diester dicarboxylates (e.g., dibasic esters, such as dialkyl adipate, dialkyl glutarate, dialkyl succinate), dialkyl carbonate, organo-nitriles, phthalate esters, propylene glycol derivatives with ethoxylation and/or propoxylation, alkoxytriglycols and other glycols such as methoxytriglycol, ethoxytriglycol, butoxytriglycol, hexyltriglycol, propylene glycol methyl ether acetate, dipropylene glycol methyl ether acetate, dipropylene glycol n-butyl ether, propylene glycol n-butyl ether, dipropylene glycol n-propyl ether, propylene glycol n-propyl ether, dipropylene glycol methyl ether, tripropylene glycol methyl ether, methanol, ethanol, butyl 3-hydroxybutyrate, isopropyl alcohol, ethylhexylglycerol, branched or unbranched diols, charged or uncharged non-surfactant emulsifying agents, polar protic solvents, polar aprotic solvents, diethylene glycol monobutyl ether, diethylene glycol monoethyl ether, butyl pyrrolidone, and mixtures thereof.

Peroxygen Stabilizers and Chelating Agents

An effective amount of one or more peroxygen stabilizers can be included in embodiments of the disclosure to enhance the stability of peroxygen compounds in solution. Some of these stabilizers are also classified as chelating agents such as poly-phosphonic acid chelating agents and salts thereof. Poly-phosphonic acid chelating agents mean chelating agents that contain more than one phosphonate or phosphonic acid group in each of their molecules.

Examples of peroxygen stabilizers include ethylenediaminetetraacetic acid (EDTA), diethylenetriaminepentaacetic acid (DTPA), N-(hydroxyethyl)-ethylene diaminetriacetic acid (HEDTA), nitrilotriacetic acid (NTA), 2-hydroxyethyliminodiacetic acid (HEIDA), benzoic acid, aminobenzoic acid, citric acid, iminodisuccinic acid, polyaspartic acid, phosphoric acid, tripolyphosphate, 1-hydroxyethylidene-1, 1-diphosphonic acid, amino tri(methylene phosphonic acid), diethylenetriaminepenta (methylene phosphonic acid), 2-hydroxy ethylimino bis(methylene phosphonic acid), ethylene diamine tetra(methylene phosphonic acid), hexamethylenediaminetetra (methylene phosphonic) acid and salts thereof.

The peroxygen stabilizers can be present in a concentration of from about 0.005, 0.1, 1, 5, 10, or 15 wt % and/or up to about 49, 40, 30, 20, 17.5, 12.5, 7.5, or 2.5 wt %.

Hydrotropes

The solution of the disclosure can include one or more hydrotropes to enhance the phase stability and solubility of its constituents. These compounds may include, but are not limited to, salts of aryl and alkylaryl sulfonic acids such as xylene sulfonic acid, cumene sulfonic acid, toluene sulfonic acid. Other hydrotropes include polyether phosphate esters, alkyl sulfates, alkyl and alkylaryl sulfonates, diphenyloxide disulfonates, and benzoic acid salts.

The hydrotrope can be present in a concentration of from about 0.1, 1, 3, 5, 10, or 20 wt % and/or up to about 25, 15, 8, 4, or 1.5 wt %.

Additional Ingredients

The present inventive compositions can include an effective amount of one or more additional ingredients as would be apparent to the person skilled in the art, including without limitation, pigments and dyes, fragrances, rheology modifiers, corrosion inhibitors, foaming agents, other skin conditioning agents or emollients, softening agents, anti-static agents, anti-wrinkling agents, dye transfer inhibition/color protection agents, odor removal/odor capturing agents, buffering agents, builders, enzymes, brighteners, radical scavengers, preservatives, soil shielding/soil releasing agents, ultraviolet light protection agents, water repellency agents, anti-pilling agents, souring agents, allergicides, surfactants and mixtures thereof. The surfactants that can be included are those anionic, nonionic, and cationic surfactants that are compatible with the peroxygen compounds used in the present compositions. Exemplary nonionic surfactants are those disclosed in U.S. Pat. No. 8,871,807 to Gohl et al. (these surfactants are incorporated herein by reference).

The dye(s) can be present in a concentration of from about 0.0002, 0.05, 1, 2, or 3 and/or up to about 5, 3, 2, 1, 0.5 or 0.01 wt %. Fragrances can be present in a concentration of from about 0.01, 0.5, 1, or 5 wt % and/or up to about 7, 3, 2, or 0.2 wt %. Rheology modifiers, including but not limited to xanthan gum or guar gum, can be present in a concentration of from about 0.02, 0.5, 1, 5, or 10 wt %, and/or up to about 15, 7, 3, 0.7, 0.1, or 0.02 wt %. Foaming agents, including but not limited to siloxanes, low-solubility oils, low-HLB nonionic surfactants, can be present in a concentration of from about 0.001, 0.1, 0.5, 2, 4, 5, or 7 wt %, and/or up to about 10, 8, 5, 4, or 3 wt %. Buffering agents can be present in a concentration of from about 0.01, 0.5, 1, 5, or 7 wt %, and/or up to about 10, 5, 3, 0.1, or 0.05 wt %. Builders can be present in a concentration of from about 0.01, 0.5, 2, 4, or 5 wt %, and/or up to about 8, 3, 1, or 0.1 wt %. Soil suspenders can be present in a concentration of from about 0.01, 0.5, 2, 5, or 10 wt %, and/or up to about 15, 8, 4, 1, or 0.1 wt %. Radical scavengers can be present in a concentration of from about 0.005, 0.5, 1, 5, or 15 wt %, and/or up to about 20, 10, 3, 0.1, or 0.01 wt %.

As mentioned above, compositions or solutions according to the disclosure can be formulated in concentrated or solid form (e.g. tablets, powder, etc.), as well as in multi-part systems wherein various components are kept separate. For example, the compositions can be implemented in a two-part system wherein a liquid component is present in one part and a solid component is present in the other part. Solutions according to the disclosure can be packaged in a dispenser, such as a spray dispenser, or another suitable dispenser package.

Test Results

Embodiments of the disclosure were prepared and tested for their peroxygen stability and antimicrobial efficacy. All the compositions disclosed herein demonstrated suitable peroxygen stability for at least one year of shelf life. Antimicrobial tests were done using standard methods maintained by the European Committee for Standardization, including the EN1499, EN1276, EN1650, EN13727 and EN13624 test methods. The efficacy of the compositions against various microorganisms is expressed below in terms of log 10 reduction of the original microbial titer's population.

The following ingredients were used in the tested solutions.

Peroxygen Compound
  Hydrogen Peroxide—35% wt solution available from Solvay S.A.
Amine Oxide Surfactant
  Lauramine Oxide—30% wt solution from Solvay S.A.
Solvent/Cyclic Alcohol
  Phenoxyethanol—100% wt compound from BASF
Skin Conditioning Agents
  1,3 Butylene Glycol—100% wt compound from Kemcare
  Glycerin—100% wt compound from Made-King Roinson&Co. Ltd.

Hexylene Glycol—100% wt solution from Kemcare

Inorganic Salt
Sodium Chloride—100% wt compound from Univar

Inorganic Acid/Peroxygen Stabilizer
Phosphoric acid—75% wt solution from Univar

Nonionic Surfactant
Lauryl Glucoside—50% to 75% solution from BASF

EXAMPLES

Solutions A and B are summarized in Table 1 below in which the amount of each ingredient is expressed in terms of wt % based on the actual active concentration in solution. These solutions were assessed for skin and eye irritation using standard European test methods. The antimicrobial efficacy of both solutions against yeast (*C. albicans*) was tested using the EN13624 test method. The antimicrobial efficacy of both solutions against the *mycobacterium M. smegmatis* was tested using the ASTM E2197 method.

TABLE 1

| Ingredients | Solution A | Solution B |
| --- | --- | --- |
| Lauramine Oxide | 1.00 | 1.00 |
| Lauryl Glucoside | 1.50 | 1.50 |
| Butylene Glycol | — | 3 |
| Hexylene Glycol | 3 | — |
| Glycerin | 3.55 | 3.55 |
| Phosphoric acid | 0.82 | 0.82 |
| Phenoxyethanol | 5.00 | 5.00 |
| Hydrogen Peroxide | 2.00 | 2.00 |
| pH | 2.25-2.50 | 2.25-2.50 |
| Redox Potential | 257 mV | 250 mV |
| Skin Irritation | Non-irritant | Non-irritant |
| Eye Irritation | Non-irritant | Non-irritant |
| Efficacy against *C. albicans* ($log_{10}$ reduction) | >4.2 | >4.2 |
| Efficacy against *M. smegmatis* ($log_{10}$ reduction) | >6.08 | >6.08 |

Solutions A and B are according to the present disclosure. Both solutions meet eye and skin safety standards and are effective against the yeast *C. albicans* and the *mycobacterium M. smegmatis*.

Although the present compositions are useful as skin disinfectants, they are also useful to reduce microbes in a wide variety of other applications, such as in disinfection, sanitization, sterilization, cleaning, bleaching, water and soil treatment, petroleum extraction and refinery, mining, odor control, and food processing applications. The solution can be used on animate and inanimate surfaces, including, without limitation, fur, hair, mucous membranes, hard and soft surfaces (including floors, countertops, carpets, textiles), porous and non-porous surfaces, tools and devices (including medical devices), animals, plants, and animal and plant matter, and combinations thereof.

The above description of embodiments is by way of example only and shall not be construed to limit the scope of the disclosure described and claimed herein. The person skilled in the art will appreciate that variations to the aforementioned embodiments are possible without departing from the scope of the disclosure.

We claim:

1. A skin-compatible antimicrobial solution, comprising:
    hydrogen peroxide in an amount of from about 2 to about 3.8 wt %;
    at least one aromatic monohydroxy alcohol selected from phenoxyethanol, phenethyl alcohol, benzyl alcohol, or any mixture thereof in an amount of from about 1.5% up to about 7% wt;
    at least one amine oxide amphoteric surfactant in an amount of from about 0.5% up to about 5% wt;
    at least one polyol-based skin conditioning agent in an amount of from about 2% up to about 10 wt %;
    an effective amount of at least one pH adjusting agent effective to adjust the pH of the solution to from about 2 to about 3; and
    water;
    wherein the solution has a redox potential value in the range of 220 to 280 mV, is readily biodegradable, and is free of aromatic carboxylic acids, inorganic salts, quaternary ammonium compounds, volatile aliphatic monohydroxy alcohols, and halogen containing compounds.

2. The solution of claim 1, wherein the at least one aromatic monohydroxy alcohol is phenoxyethanol, benzyl alcohol, or a mixture thereof.

3. The solution of claim 2, wherein phenoxyethanol is present.

4. The solution of claim 1, wherein the at least one amine oxide surfactant is selected from lauramine oxide, cocamidopropyl amine oxide, cocamine oxide, coamidomethyl amine oxide, coamidopropyl amine oxide, coco dipropylamine oxide, coco methylamine oxide, cetylamine oxide, decylamine oxide, myristamine oxide, isodecyloxypropylamine oxide, α,α'-[(oxidoimino)bis(methyl-2,1-ethanediyl]) bis[omegahydroxypoly[oxy (methyl-2,1-ethanediyl]), N-[3-(C9-11-isoalkyl oxy) propyl], tetradecyldimethylamine oxide, ethoxy tallow amine oxides, propoxy tallow amine oxides, or any mixture thereof.

5. The solution of claim 4, wherein lauramine oxide is present.

6. The solution of claim 1, wherein the at least one polyol-based skin conditioning agent is selected from butylene glycol, hexylene glycol, or a mixture thereof.

7. The solution of claim 1, further comprising at least one additional skin conditioning agent selected from glycerin, polyglycerin, diglycerides, triglycerides, phospholipids, castor oil, allantoin, cationic polymers, lanolin, cetyl alcohol, ceramides, essential fatty acids, non-volatile monohydroxy alcohols, gamma-linolenic acid, linoleic acid, gamma-linoleic acid, tocopherols, glycerol ethers, ascorbates, glucose-ethers, vegetable oils, amino acids, mineral oils, or any combination thereof.

8. The solution of claim 1, wherein glycerin is present.

9. The solution of claim 1, further comprising a nonionic surfactant.

10. The solution of claim 9, wherein the nonionic surfactant is lauryl glycoside.

11. The solution of claim 1, further comprising a peroxygen stabilizer, an inorganic acid, or a combination thereof.

12. The solution of claim 11, wherein phosphoric acid is present.

13. A concentrated antimicrobial solution which, upon dilution, yields the antimicrobial solution of claim 1.

14. A method of reducing the microbial load of a surface contaminated with microorganisms, the method comprising:
    providing a solution according to claim 1; and
    applying the solution to the surface for a contact time sufficient to reduce the microbial load by at least 1 log 10.

15. The method of claim 14, wherein the contact time is less than two minutes, and wherein the reduction of microbial load is by at least 3 log 10.

16. The method of claim 14, wherein the surface is skin.

17. The solution of claim 1, wherein the solution further comprises at least one ingredient selected from pigments, dyes, fragrances, rheology modifiers, foaming agents, softening agents, anti-wrinkling agents, odor removal agents, odor capturing agents, anionic surfactants, nonionic surfactants, buffering agents, builders, chelating agents, peroxygen stabilizers, radical scavengers, preservatives, soil shielding agents, soil releasing agents, ultraviolet light protection agents, allergicides, or any combination thereof.

18. The solution of claim 1, wherein the solution fulfills at least one of the following:
   (a) the at least one aromatic monohydroxy alcohol is phenoxyethanol, benzyl alcohol, or a mixture thereof;
   (b) the at least one amine oxide surfactant is selected from lauramine oxide, cocamidopropyl amine oxide, cocamine oxide, coamidomethyl amine oxide, coamidopropyl amine oxide, coco dipropylamine oxide, coco methylamine oxide, cetylamine oxide, decylamine oxide, myristamine oxide, isodecyloxypropylamine oxide, $\alpha,\alpha'$-[(oxidoimino)bis(methyl-2,1-ethanediyl]) bis[omegahydroxypoly[oxy(methyl-2,1-ethanediyl]), N-[3-(C9-11-isoalkyl oxy) propyl], tetradecyldimethylamine oxide, ethoxy tallow amine oxides, propoxy tallow amine oxides, or any mixture thereof;
   (c) the at least one polyol-based skin conditioning agent is selected from butylene glycol, hexylene glycol, or a mixture thereof.

19. A concentrated antimicrobial solution which, upon dilution, yields the solution of claim 18.

20. A method of reducing the microbial load of a surface contaminated with microorganisms, the method comprising:
   providing a solution according to claim 18, and
   applying the solution to the surface for a contact time sufficient to reduce the microbial load by at least 1 $\log_{10}$.

* * * * *